US007829658B2

(12) United States Patent
Duffy et al.

(10) Patent No.: US 7,829,658 B2
(45) Date of Patent: Nov. 9, 2010

(54) MONO-, OLIGO- AND POLYMERS OF THIENOTHIAZOLE

(75) Inventors: Warren Duffy, Southampton (GB);
Martin Heeney, Southampton (GB);
Iain McCulloch, Southampton (GB)

(73) Assignee: Merck Patent Gesellschaft, Darmstadt (DE)

( * ) Notice: Subject to any disclaimer, the term of this patent is extended or adjusted under 35 U.S.C. 154(b) by 170 days.

(21) Appl. No.: 11/916,944

(22) PCT Filed: May 11, 2006

(86) PCT No.: PCT/EP2006/004422

§ 371 (c)(1),
(2), (4) Date: Dec. 7, 2007

(87) PCT Pub. No.: WO2006/131185

PCT Pub. Date: Dec. 14, 2006

(65) Prior Publication Data

US 2008/0200634 A1     Aug. 21, 2008

(30) Foreign Application Priority Data

Jun. 9, 2005    (EP)    ................................ 05012414

(51) Int. Cl.
*C08G 75/10*       (2006.01)
(52) U.S. Cl. .................. 528/377; 528/363; 528/128; 528/10; 548/153
(58) Field of Classification Search ................ 528/363, 528/377, 128, 10, 153
See application file for complete search history.

(56) References Cited

U.S. PATENT DOCUMENTS 5,851,425 A     12/1998    Buchecker et al.
2005/0080219 A1*   4/2005    Koller et al. .................. 528/73

OTHER PUBLICATIONS

Kim In Tae et al, "A new low bandgap conducting polymer"2003, Polymer Preprints (American Chemical Society Division of Polymer Chemistry), 44(1), 1163-1164 coden: ACPPAY; XP009071312.
Rangnekar D W et al, "Synthesis of novel c-hetero-fused thiophene derivatives", Journal of Heterocyclic Chemistry, 28(5), 1449-51 coden: JHTCAD; 1991, XP002395735.
Shafiee A et al, "Selenium heterocycles . XXXIX. Synthesis of thieno[3,4-d]thiazole, thieno[3,4-d]selenazole, selenolo[3,4-d]thiazole and selenolo[3,4-d]selenazole" Journal of Heterocyclic Chemistry, 26(3), 709-11 coden: JHTCAD; 1989, XP002395736.
Shafiee A et al, "Selenium heterocycles. XXVII. Synthesis of thieno[2,3-d]thiazole and selenolo[3,4-d]thiazole. Two novel heterocycles" Journal of Heterocyclic Chemistry, 15(8), 1455-7 coden; JHTCAD; 1978, XP002395737.
Pomerantz M et al, "Poly(2-decylthieno[3,4-b]thiophene-4, 6-diyl). A new low band gap conducting polymer", Macromolecules, ACS, Washington, DC, US, vol. 34, 2001, pp. 1817-1822, XP002329966.
Polymer Preprints, American Chemical Society, US, vol. 45, No. 1, 2004, pp. 218-219, XP009070865.
Roncali J, "Synthetic Principles for Bandgap Control in Linear pi-Conjugated Systems" Chemical Reviews, vol. 97, No. 1, 1997, pp. 173-205, XP002395738.

* cited by examiner

*Primary Examiner*—Randy Gulakowski
*Assistant Examiner*—Shane Fang
(74) *Attorney, Agent, or Firm*—Millen, White, Zelano & Branigan, P.C.

(57) ABSTRACT

The invention relates to novel mono-, oligo- and polymeric compounds comprising thienothiazole groups, to their use as semiconductors or charge transport materials, in optical, electro-optical or electronic devices, and to optical, electro-optical or electronic devices comprising the novel compounds.

29 Claims, No Drawings

MONO-, OLIGO- AND POLYMERS OF THIENOTHIAZOLE

FIELD OF INVENTION

The invention relates to novel mono-, oligo- and polymeric compounds comprising thienothiazole groups. The invention further relates to their use as semiconductors or charge transport materials, in optical, electro-optical or electronic devices. The invention further relates to optical, electro-optical or electronic devices comprising the novel compounds.

BACKGROUND AND PRIOR ART

In recent years there has been growing interest in the use of polymers for electronic applications. One particular area of importance is organic photovoltaics (OPV). Polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based devices are achieving efficiencies up to 4-5%. This is appreciably lower than the efficiencies attainable by inorganic devices, which are typically up to 25%.

The class of polymers currently achieving the highest efficiencies in OPV devices are the poly(3-alkyl-thiophenes). The most commonly used example is poly(3-hexyl-thiophene), P3HT, due to its broad availability and good absorption characteristics. P3HT absorbs strongly over the 480-650 nm range, with a peak maximum absorption at 560 nm. This means a significant portion of the light emitted by the sun is not being absorbed.

In order to improve the efficiency of OPV devices, polymers are required that absorb more light from the longer wavelength region (650-800 nm). For this purpose, polymers are desired which have a low band gap, preferably less than 1.9 eV, whereas for example P3HT has a band gap of ~2.0 eV.

Low band gaps are attained in polyaromatic conjugated polymers with a high quinoidal contribution. Poly(thiophene), for example, can exist in both the aromatic and quinoidal state as shown below:

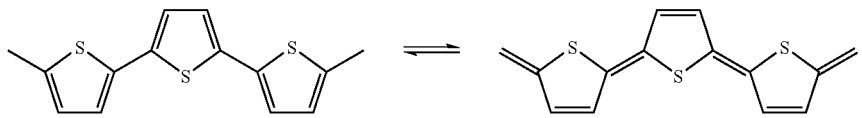

A quinoidal structure reduces the torsion between adjacent rings, which results in a more planar polymer backbone leading to an extension of the effective conjugation length. It is generally observed in conjugated polymers that an increase in the conjugation length results in a decrease of the bandgap.

The quinoidal state can be stabilised by fusing an aromatic ring to the thiophene backbone. The fused ring is only fully aromatic when the backbone is in the quinoidal state. This means there is a strong desire for the polymer to be in the quinoidal state. Previous work (see J. Roncali, Chem. Rev., 1997, 97, 173 and references cited therein) has demonstrated the use of a benzo or naptho fused thiophene, as shown below, to reduce the bandgap:

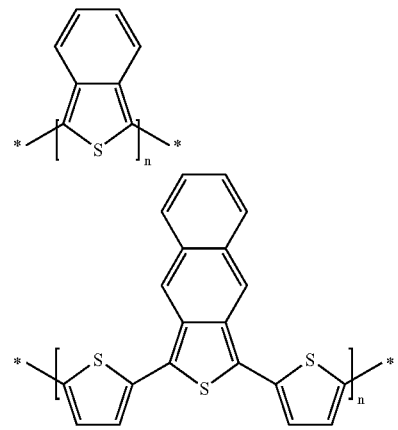

However, in these cases the fused six-member ring can cause steric strain by interaction with the neighbouring thiophene monomers. This can result in undesirable twists in the backbone, and a concurrent reduction in effective conjugation. By fusing a five-member ring steric interactions are reduced. One related example as shown below demonstrates the use of a fused thiophene ring:

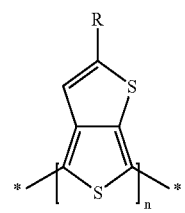

However, this type of structure is synthetically very complex (M. Pomerantz, X. Gu and S. X. Zhang, Macromolecules, 2001, 34 (6), 1817).

It is an aim of the present invention to provide new materials for use as semiconductors or charge transport materials, which have the desired properties as described above, especially a low band gap, high charge mobility, good processibility and oxidative stability, and furthermore are easy to synthesize. Another aim of the invention is to provide new semiconductor and charge transport components, and new and improved electrooptical, electronic and luminescent devices comprising these components. Other aims of the invention are immediately evident to those skilled in the art from the following description.

The inventors have found that these aims can be achieved by providing mono-, oligo- and polymers as claimed in the present invention, which comprise a 2-substituted thieno[3,4-d]thiazole-6,4-diyl unit of the following structure:

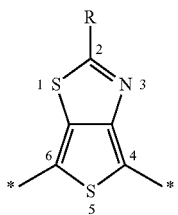

The materials according to the present invention comprise a five-membered thiazole ring that is fused to the thiophene. This does not only increase the quinoidal contribution compared to thiophene, but, being more electron deficient, it also helps to improve the stability by withdrawing electron density as shown below:

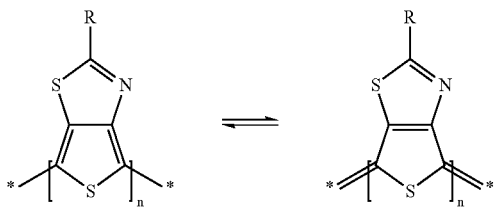

I. T. Kim, S. W. Lee and J. Y. Lee, Polymer Preprints, 2003, 44(1), 1163 disclose the homopolymer poly(2-nonyl)thieno[3,4-d]thiazole:

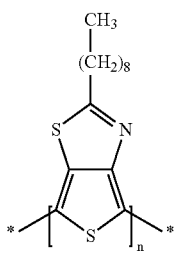

The reference gives details on the synthesis and characterisation of the homopolymers for use as low band gap conducting polymers. The homopolymer absorbs in the 650-800 nm region, with a peak maximum absorption at 725 nm. The band gap for this polymer, calculated using the bandedge from the UV-vis-NIR and cyclic voltammetry, was found to be 1.3 eV and 1.26 eV respectively. However, the polymer is prepared electrochemically, which is not conducive to large scale preparations. Moreover, copolymers are not described in this reference.

SUMMARY OF THE INVENTION

The invention relates to monomeric, oligomeric and polymeric compounds comprising one or more thieno[3,4-d]thiazole-6,4-diyl groups, that are optionally substituted in 2-position, with the proviso that homopolymers of 2-nonyl-thieno[3,4-d]thiazole-6,4-diyl are excluded.

The invention further relates to the use of the compounds of formula I as semiconducting, charge transport or light-emitting materials.

The invention further relates to a semiconducting, electroluminescent or charge transport material, component or device comprising at least one compound of formula I.

The invention further relates to the use of compounds of formula I as charge-transport, semiconducting, electrically conducting, photoconducting or light-emitting material in optical, electrooptical or electronic components or devices, organic photovoltaic devices (OPV), organic field effect transistors (OFET), integrated circuitry (IC), thin film transistors (TFT), flat panel displays, radio frequency identification (RFID) tags, electroluminescent or photoluminescent devices or components, organic light emitting diodes (OLED), backlights of displays, sensor devices, charge injection layers, Schottky diodes, planarising layers, antistatic films, conducting substrates or patterns, electrode materials in batteries, photoconductors, electrophotographic applications, electrophotographic recording, organic memory devices, alignment layers, cosmetic or pharmaceutical compositions, biosensors, biochips, or for detecting and discriminating DNA sequences.

The invention further relates to an optical, electrooptical or electronic device, OPV device, OFET, integrated circuit (IC), TFT, OLED or alignment layer comprising a compound, semiconducting or charge transport material, component or device according to the invention.

The invention further relates to a TFT or TFT array for flat panel displays, radio frequency identification (RFID) tag, electroluminescent display or backlight comprising a compound, semiconducting or charge transport material, component or device or a FET, IC, TFT or OLED according to the invention.

The invention further relates to a security marking or device comprising a FET or an RFID tag according to the invention.

DETAILED DESCRIPTION OF THE INVENTION

In the foregoing and the following, "thieno[3,4-d]thiazole-6,4-diyl" means the following group

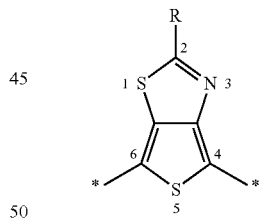

and "thieno[3,4-d]thiazole-4,6-diyl" means the following group

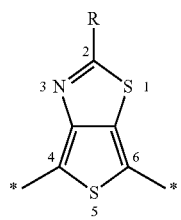

(wherein R is H or a substituent).

The terms 'alkyl', 'aryl' etc. also include multivalent species, for example alkylene, arylene etc. The term 'aryl' or 'arylene' means an aromatic hydrocarbon group or a group derived from an aromatic hydrocarbon group. The term 'heteroaryl' or 'heteroarylene' means an 'aryl' or 'arylene' group comprising one or more hetero atoms.

The compounds according to the invention are especially useful as charge transport or semiconductor materials. Introduction of alkyl side chains in 2-position of the thieno[3,4-d]thiazole group further improves solubility and solution processibility especially for the polymers.

The polymers according to the present invention can be homopolymers or alternating, random or block copolymers. Particularly preferred are copolymers, especially regular alternating copolymers.

There are a number of advantages for using copolymers containing the 2-substituted thieno[3,4-d]thiazole ring. Firstly, the low band gap nature of this fused thiophene ring structure can help increase the absorption of polymers in the longer wavelength region. Secondly, co-monomers can be used to improve device properties, such as the open and short circuit voltages, and also processing properties, such as solubility. Co-monomers help the molecule to pack efficiently, and therefore afford polymers with high mobility, which is also important as this reduces charge recombination. Recombination is another factor that leads to poor device efficiencies in OPVs The regioregularity in the polymers of the present invention is preferably at least 90%, in particular 95% or more, very preferably 98% or more, most preferably from 99 to 100%.

Regioregular polymers are advantageous as they show strong interchain pi-pi-stacking interactions and a high degree of crystallinity, making them effective charge transport materials with high carrier mobilities.

Further preferred are mono-, oligo- and polymers that are mesogenic or liquid crystalline, in particular polymers forming calamitic phases, and polymerisable monomers comprising one or more groups P-Sp- and forming calamitic phases.

The monomeric, oligomeric and polymeric compounds are preferably selected of formula I

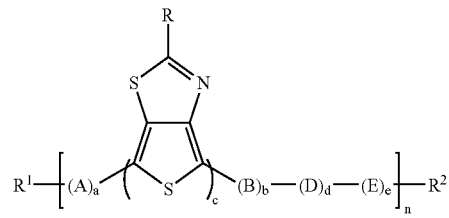

I wherein
R is in case of multiple occurrence independently of one another H, halogen, optionally substituted aryl or heteroaryl, P-Sp-, P*-Sp-, or straight chain, branched or cyclic alkyl with 1 to 20 C-atoms, which is optionally mono- or polysubstituted by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —O—CO—O—, —S—CO—, —CO—S—, —$CX^1$=$CX^2$— or —C≡C— in such a manner that O and/or S atoms are not linked directly to one another, $R^0$ and $R^{00}$ are independently of each other H, aryl or alkyl with 1 to 12 C-atoms, $X^1$ and $X^2$ are independently of each other H, F, Cl or CN, P is a polymerisable group, P* is a group that can be converted to or substituted by a polymerisable group P, Sp is a spacer group or a single bond, A, B and D are independently of each other, and in case of multiple occurrence independently of one another, —$CX^1$=$CX^2$—, —C≡C— or an arylene or heteroarylene group that is optionally substituted with one or more groups R, E is thieno[3,4-d]thiazole-4,6-diyl or thieno[3,4-d]thiazole-6,4-diyl that is optionally substituted in 2-position with R, a, b, c, d, e are independently of each other 0, 1, 2 or 3, with at least one of c and e being 1, n is an integer ≧1, wherein the recurring units are identical or different, with the proviso that compounds wherein a=b=d=e=0, c=1 and R is n-nonyl are excluded.

Especially preferred are compounds of formula I1

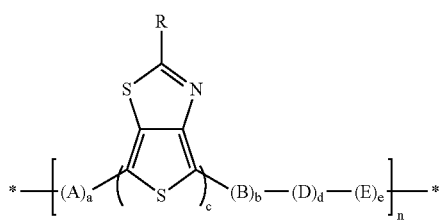

I1 wherein R, A, B, D, E, a-e and n have the meanings of formula I, $R^1$ and $R^2$ independently of each other have one of the meanings of R or denote —$Sn(R^0)_3$, —$B(OR')(OR")$, —$CH_2Cl$, —CHO, —CH=$CH_2$ or —$SiR^0R^{00}R^{000}$, $R^0$, $R^{00}$, $R^{000}$ are independently of each other H, aryl or alkyl with 1 to 12 C-atoms, R' and R" are independently of each other H or alkyl with 1 to 12 C-atoms, or OR' and OR" together with the boron atom form a cyclic group having 2 to 20 C atoms.

Especially preferred are compounds of formula I and I1 wherein n is an integer from 2 to 5000, preferably from 10 to 5000, very preferably from 100 to 1000, n=1, n≧2, the molecular weight (Mw) is from 5000 to 300,000, in particular from 20,000 to 100,000, a and/or b are 1, d is 0, c is 1 or 2, e is 0, R is halogen, optionally substituted aryl or heteroaryl, P-Sp-, P*-Sp-, or straight chain, branched or cyclic alkyl with 9 to 20 C-atoms, which is optionally mono- or polysubstituted by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —O—CO—O—, —S—CO—, —CO—S—, —CX¹=CX²— or —C≡C— in such a manner that O and/or S atoms are not linked directly to one another, R is selected from $C_1$-$C_{20}$-alkyl, $C_1$-$C_{20}$-alkoxy, $C_2$-$C_{20}$-alkenyl, $C_2$-$C_{20}$-alkynyl, $C_1$-$C_{20}$-thioalkyl, $C_1$-$C_{20}$-silyl, $C_1$-$C_{20}$-siloxy, $C_1$-$C_{20}$-ester, $C_1$-$C_{20}$-amino, $C_1$-$C_{20}$-fluoroalkyl, and optionally substituted aryl or heteroaryl, very preferably $C_1$-$C_{20}$-alkyl or $C_1$-$C_{20}$-fluoroalkyl, A, B and/or D denote

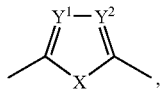

wherein $Y^1$ and $Y^2$ are selected from CH, CR or N and X is S or O, very preferably thiophene-2,5-diyl that is optionally substituted by one or two groups R different from H or phenylene-1,4-diyl that is optionally substituted by one, two, three or four groups R different from H, A, B and/or D is —CX¹=CX²—, —C≡C— or a single bond, preferably —CH=CH— or a single bond, P* is —OH or —O—Si—$R^0R^{00}R^{000}$, preferably wherein $R^0$, $R^{00}$ and $R^{000}$ are identical or different groups selected from aryl or $C_{1-12}$-alkyl, preferably $C_1$-$C_B$-alkyl, like methyl, ethyl, isopropyl, tert-butyl or phenyl, $R^7$ and $R^8$ are selected from H, halogen, $Sn(R^0)_3$, B(OR')(OR''), $CH_2Cl$, CHO, CH=$CH_2$, $SiR^0R^{00}R^{000}$ and optionally substituted aryl or heteroaryl, n is 1 and one or both of $R^7$ and $R^8$ are halogen which is preferably Br, Cl or I, $Sn(R^0)_3$, B(OR')(OR''), $CH_2Cl$, CHO, CH=$CH_2$ or $SiR^0R^{00}R^{000}$, R is P-Sp-, n is 1 and one or both of $R^7$ and $R^8$ are P-Sp- or P*-Sp-.

If A, B or D is arylene or heteroarylene, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more groups L, with L being selected from F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O—, —S—CO—, —CO—S—, —CH=CH— or —C≡C— in such a manner that O and/or S atoms are not linked directly to one another.

Preferred arylene or heteroarylene groups are selected from phenylene in which, in addition, one or more CH groups may be replaced by N, or naphthalene, alkyl fluorene, oxazole, thiophene, selenophene, dithienothiophene, wherein all these groups are optionally mono- or polysubstituted with L as defined above.

Further preferred arylene or heteroarylene groups groups are 1,4-phenylene, 2,5-pyridine, 2,5-pyrimidine, p,p'-biphenyl, naphthalene-2,6-diyl, thiophene-2,5-diyl, selenophene-2,5-diyl, thiophene-2,5-diyl or selenophene-2,5-diyl, fluorene-2,7-diyl, 2,2'-dithiophene, 2,2'-dithiophene, thieno[2,3-b]thiophene-2,5-diyl, thieno[3,2-b]thiophene-2,5-diyl, fluorinated benzo[1,2-b:4,5-b']dithiophene, 2,5-thiazole, 2,5-thiadiazole, thieno[3,4-d]thiazole-4,6-diyl, thieno[3,4-d]thiazole-6,4-diyl, 2,5-oxazole and 2,5-oxadiazole, all of which are unsubstituted, or optionally fluorinated, alkylated, or mono- or polysubstituted with L as defined above.

If R is aryl or heteroaryl, it is preferably a mono-, bi- or tricyclic aromatic or heteroaromatic group with up to 25 C atoms, wherein the rings can be fused. Heteroaromatic groups contain at least one hetero ring atom preferably selected from N, O and S. The aromatic or heteroaromatic groups are optionally substituted with one or more groups L as defined above.

Especially preferred aryl and heteroaryl groups are phenyl, fluorinated phenyl, pyridine, pyrimidine, biphenyl, naphthalene, fluorene, benzo[1,2-b:4,5-b']dithiophene, thieno[3,2-b]thiophene, 2,2-dithiophene, thiazole, thieno[2,3d]thiazole and oxazole, all of which are unsubstituted, mono- or polysubstituted with L as defined above, for example fluorinated, alkylated or fluoroalkylated.

If R is an alkyl or alkoxy radical, i.e. where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Fluoroalkyl or fluorinated alkyl or alkoxy is preferably straight chain $(O)C_iF_{2i+i}$, wherein i is an integer from 1 to 20, in particular from 1 to 15, very preferably $(O)CF_3$, $(O)C_2F_5$, $(O)C_3F_7$, $(O)C_4F_9$, $(O)C_5F_{11}$, $(O)C_6F_{13}$, $(O)C_7F_{15}$ or $(O)C_8F_{17}$, most preferably $(O)C_6F_{13}$.

$CX^1$=$CX^2$ is preferably —CH=CH—, —CH=CF—, —CF=CH—, —CF=CF—, —CH=C(CN)— or —C(CN)=CH—.

Halogen is preferably F, Br or Cl.

Hetero atoms are preferably selected from N, O and S, furthermore Se, Te and As.

Especially preferred are compounds of the following formulae

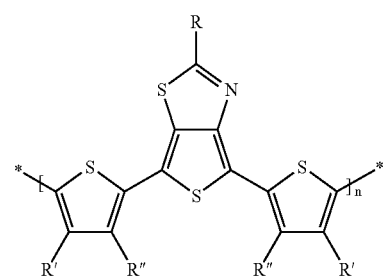

IIa

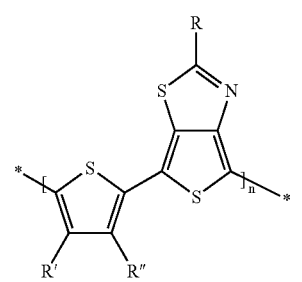

IIb

-continued

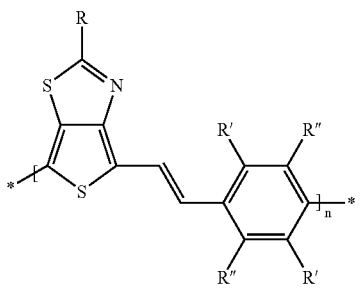
IIc

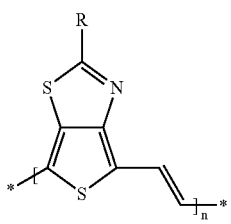
IId

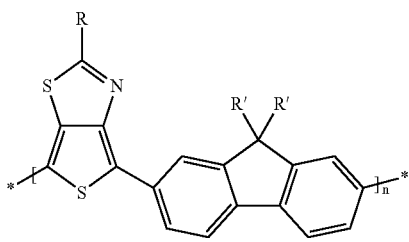
IIe

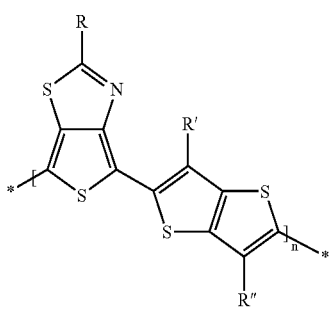
IIf

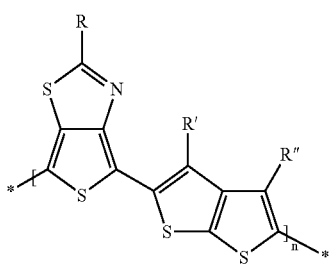
IIg

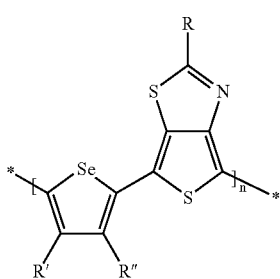
IIh

-continued

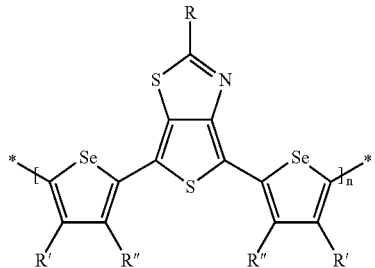
IIi wherein R and n have the meanings of formula I and R' and R" have independently of each other one of the meanings of R given in formula 1.

Especially preferred are compounds of formula IIa and IIf, wherein R' are H and R" are different from H.

The polymerisable group P is a group that is capable of participating in a polymerisation reaction, like radicalic or ionic chain polymerisation, polyaddition or polycondensation, or capable of being grafted, for example by condensation or addition, to a polymer backbone in a polymeranaloguous reaction. Especially preferred are polymerisable groups for chain polymerisation reactions, like radicalic, cationic or anionic polymerisation. Very preferred are polymerisable groups comprising a C—C double or triple bond, and polymerisable groups capable of polymerisation by a ring-opening reaction, like oxetanes or epoxides.

Very preferably the polymerisable group P is selected from $CH_2=CW^1$—COO—, $CH_2=CW^1$—CO—,

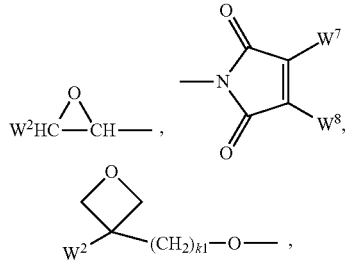

$CH_2=CW^2$—$(O)_{k1}$—, $CH_3$—CH=CH—I—, $(CH_2=CH)_2$CH—OCO—, $(CH_2=CH$—$CH_2)_2$CH—OCO—, $(CH_2=CH)_2$CH—O—, $(CH_2=CH$—$CH_2)_2$N—, $(CH_2=CH$—$CH_2)_2$N—CO—, HO—$CW^2W^3$—, HS—$CW^2W^3$—, $HW^2$N—, HO—$CW^2W^3$—NH—, $CH_2=CW^1$—CO—NH—, $CH_2=CH$—$(COO)_{k1}$-Phe-$(O)_{k2}$—, $CH_2=CH$—$(CO)_{k1}$-Phe-$(O)_{k2}$—, Phe-CH=CH—, HOOC—, OCN—, and $W^4W^5W^6$Si—, with $W^1$ being H, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Especially preferred groups P are $CH_2=CH$—COO—, $CH_2=C(CH_3)$—COO—, $CH_2=CH$—, $CH_2=CH$—O—, $(CH_2=CH)_2$CH—OCO—, $(CH_2=CH)_2$CH—O—,

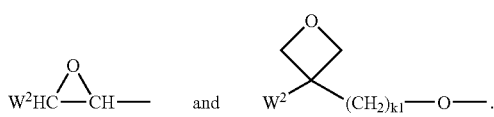

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As spacer group Sp all groups can be used that are known for this purpose to the skilled in the art. The spacer group Sp is preferably of formula Sp'-X, such that P-Sp- is P-Sp'-X— and P*-Sp- is P*-Sp'-X—, wherein
Sp' is alkylene with up to 20 C atoms which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=CH— or —C≡C— in such a manner that O and/or S atoms are not linked directly to one another,
X is —O—, —S—, —CO—, —COO—, —COO—, —O—COO—, —CO—$NR^o$—, —$NR^o$—CO—, —CO—$NR^o$—CO—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^o$—, —$CX^1$=$CX^2$—, —C≡C—, —CH=CH—COO—, —OCO—CH=CH— or a single bond, and $R^o$, $R^{oo}$, $X^1$ and $X^2$ have one of the meanings given above.
X is preferably —O—, —S—, —$OCH_2$—, —$CH_2O$—, —$SCH_2$—, —$CH_2S$—, —$CF_2O$—, $OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^o$—, —$CX^1$=$CX^2$—, —C≡C— or a single bond, in particular —O—, —S—, —C≡C—, —$CX^1$=$CX^2$— or a single bond, very preferably a group that is able to from a conjugated system, such as —C≡C— or —$CX^1$=$CX^2$—, or a single bond.

Typical groups Sp' are, for example, —$(CH_2)_p$—, —$(CH_2CH_2O)_q$—$CH_2CH_2$—, —$CH_2CH_2$—S—$CH_2CH_2$— or —$CH_2CH_2$—NH—$CH_2CH_2$— or —$(SiR^oR^{oo}$—O$)_p$—, with p being an integer from 2 to 12, q being an integer from 1 to 3 and $R^o$ and $R^{oo}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P-Sp- or P*-Sp- wherein Sp is a single bond.

In case of compounds with two groups P-Sp or P*-Sp-, respectively, each of the groups P or P* and the spacer groups Sp can be identical or different.

Another preferred embodiment relates to compounds comprising one or more groups P*-Sp-, wherein P* is a group that can be converted to or substituted by a polymerisable group P as defined above. Preferably P* is a group that is less reactive than P, for example towards spontaneous polymerisation. These compounds can be used for example as intermediates in the synthesis of polymerisable compounds of formula I having one or more groups P, or as a precursor material for polymerisable compounds which are too reactive to be stored or transported for longer periods of time. The group P* is preferably chosen such that it can easily be transformed into or substituted by a group P by known methods. For example, it can be a protected form of group P. Further preferred groups P* are for example —OH or silyl groups like —O—Si—$R^oR^{oo}R^{ooo}$, for example —O—Si$(CH_3)_3$, —O—Si-(isopropyl)$_3$, —O—Si-(phenyl)$_3$, —O—Si—$(CH_3)_2$(phenyl), —O—Si$(CH_3)_2$(tert-butyl) or the like, which can be reacted e.g. into polymerisable (meth)acrylate end groups.

SCLCPs obtained from the inventive compounds or mixtures by polymerisation or copolymerisation have a backbone that is formed by the polymerisable group P.

The mono-, oligo- and polymers of the present invention can be synthesized according to or in analogy to methods that are known or described in the examples. A typical synthetic route to prepare polymers of formula I is shown below in Scheme 1, wherein R and n are as defined in formula I.

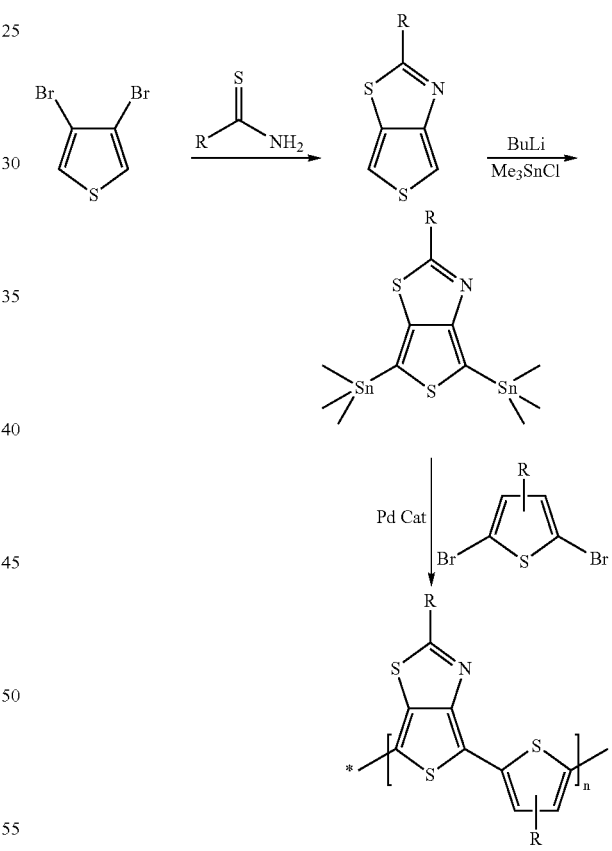

Scheme 1

The fused thiazole can be synthesized from readily available 3,4-dibromothiophene (scheme 1). Lithiation by reaction with one equivalent of an alkyl lithium reagent followed by reaction with a dialkyldisulfide or reaction with elemental sulfur followed by reaction with an alkylating agent affords a thiophene thioether. The reaction can also proceed via the organomagnesium intermediate formed by reaction with isopropylmagnesium chloride. The remaining bromo group on the thiophene thioether is then displaced with a substituted amine under the conditions described by Buchwald and co-workers (*J. Am. Chem. Soc.* 2001, p7727). The resulting amide can then be ring closed to the fused thieno[3,4-d]thiazole by deprotection of the thioether and sequential treatment with a dehydrating agent such as polyphosphonic acid. In some cases this sequence can be combined in a one pot procedure, for example treatment of a methylthioether (R'=$CH_3$) with phoshonitrillic chloride under the conditions described by Rosini and co-workers (*Synthesis* 1977, 892) results in direct formation of the thiazole.

aromatic bis(boronic ester) or aromatic bis(organotin) reagent in the presence of a palladium catalyst. Alternatively the thieno[3,4-d]thiazole can be stannylated or boroylated in the 4,6-positions by treatment with an organolithium reagent, followed by reaction with a trialkyltin halide or an alkoxyborane. The resulting thieno[3,4-d]thiazole can then be co-polymerised by reaction with a disubstituted aromatic halide in the presence of a transition metal catalyst.

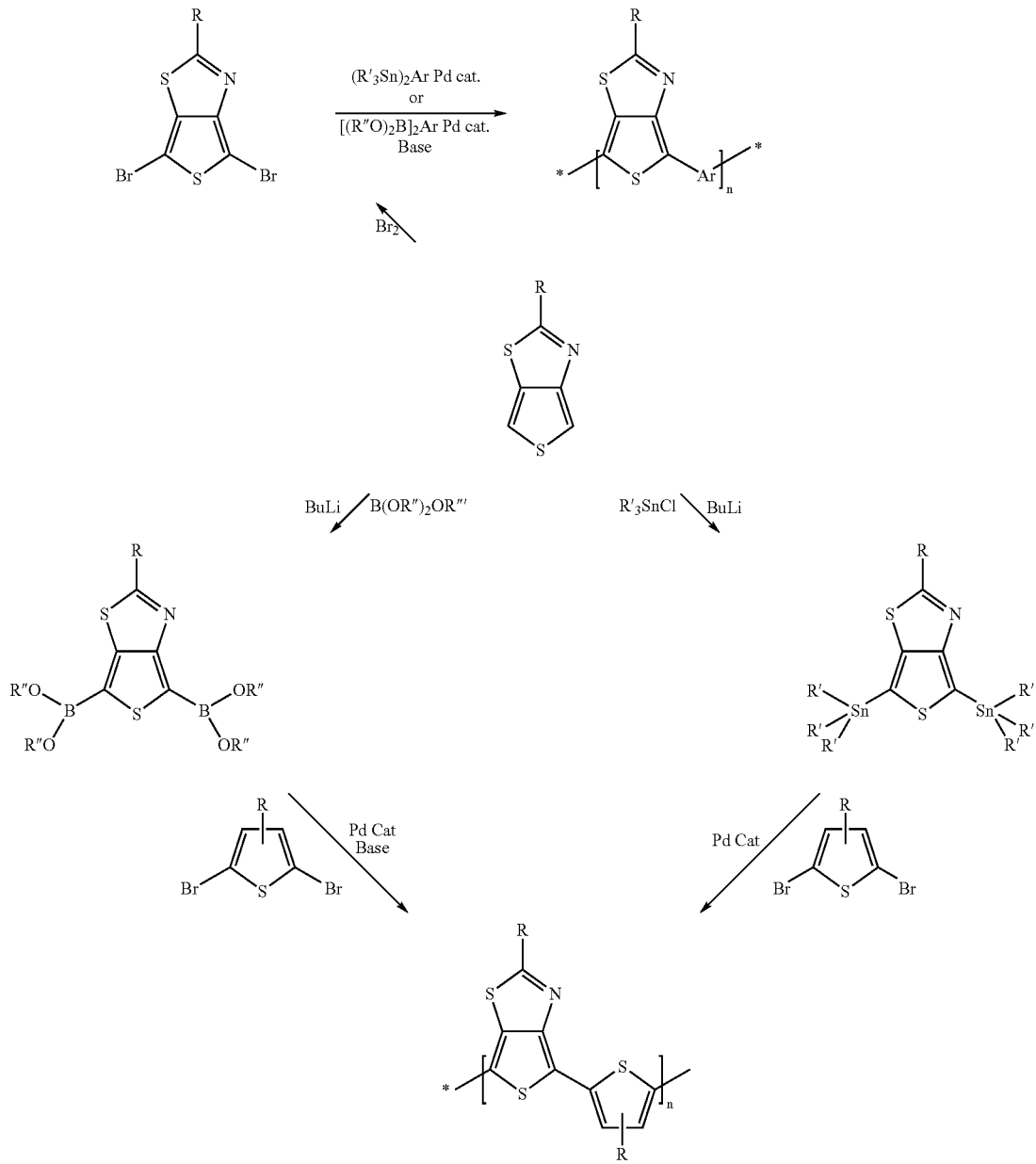

The thieno[3,4-d]thiazole can be polymerized by a number of techniques as described in scheme 2. The thieno[3,4-d]thiazole can be dibrominated in the 4,6-positions by treatment with bromine or N-bromosuccinimide. Co-polymers can then be prepared by reaction with an appropriate disubstituted A further aspect of the invention relates to both the oxidised and reduced form of the compounds and materials according to this invention. Either loss or gain of electrons results in formation of a highly delocalised ionic form, which is of high conductivity. This can occur on exposure to common dopants.

Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_5^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^+)$, $(NO_2^+)$ $(SbCl_6^-)$, $(NO_2^+)(BF_4^-)$, $AgClO_4$, $H_2IrCl_6$, $La(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

A preferred embodiment of the present invention relates to mono-, oligo- and polymers of formula I and I1 and their preferred subformulae that are mesogenic or liquid crystalline, and very preferably comprise one or more polymerisable groups. Very preferred materials of this type are monomers and oligomers of formula I or I1 and their preferred subformulae wherein n is an integer from 1 to 15 and $R^1$ and/or $R^2$ denote P-Sp-.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

For example, if a device is made from a polymerisable liquid crystal material by polymerisation in situ, the liquid crystal material preferably comprises one or more mono- or oligomers of formula I1 and its preferred subformulae wherein one or both of $R^1$ and $R^2$ denote P-Sp-. If a liquid crystal polymer is preapred first, for example by polymerisation in solution, and the isolated polymer is used to make the device, the polymer is preferably made from a liquid crystal material comprising one or more mono- or oligomers of formula I1 and its preferred subformulae wherein one of $R^1$ and $R^2$ denotes P-Sp-.

It is also possible to copolymerise the polymerisable mono-, oligo- and polymers according to the present invention with other polymerisable mesogenic or liquid crystal monomers that are known from prior art, in order to induce or enhance liquid crystal phase behaviour.

Thus, another aspect of the invention relates to a polymerisable liquid crystal material comprising one or more mono-, oligo- or polymers of the present invention as described above and below comprising at least one polymerisable group, and optionally comprising one or more further polymerisable compounds, wherein at least one of the polymerisable mono-, oligo- and polymers of the present invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred. Especially preferred are smectic A ($S_A$) phases, furthermore highly ordered smectic phases like the $S_B$, $S_E$, $S_G$ and $S_F$ phase.

Another aspect of the present invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Preferably polymerisation is carried out as in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45-66

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Mono-, oligo- and polymers comprising one or more groups P-Sp-can also be copolymerised with polymerisable mesogenic compounds to induce or enhance liquid crystal phase behaviour. Polymerisable mesogenic compounds that are suitable as comonomers are known in prior art and disclosed for example in WO 93/22397; EP 0,261,712; DE 195, 04,224; WO 95/22586 and WO 97/00600.

Another aspect of the invention relates to a liquid crystal side chain polymer (SCLCP) obtained from a polymerisable liquid crystal material as defined above by polymerisation or polymeranaloguous reaction. Particularly preferred are SCLCPs obtained from one or more monomers of formula I1 and its preferred subformulae wherein one or both, preferably one, of $R^1$ and $R^2$ are a polymerisable or reactive group, or from a polymerisable mixture comprising one or more of said monomers.

Another aspect of the invention relates to an SCLCP obtained from one or more monomers of formula I1 and its preferred subformulae wherein one or both of $R^1$ and $R^2$ are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation.

Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added, e.g., to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397, EP 0 261 712, DE 195 04 224, WO 95/22586, WO 97/00600 and GB 2 351 734. Typical non mesogenic comonomers are for example alkyl acrylates or alkyl methacrylates with alkyl groups of 1 to 20 C atoms, like methyl acrylate or methyl methacrylate.

The mono-, oligo- and polymers of the present invention are useful as optical, electronic and semiconductor materials, in particular as charge transport materials in organic photovoltaics (OPV), organic field effect transistors (OFETs), e.g., as components of integrated circuitry, ID tags or TFT applications. Alternatively, they may be used in organic light emitting diodes (OLEDs) in electroluminescent display applications or as backlight of, e.g., liquid crystal displays, as sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

OPV devices do typically consist of a thin light-absorbing layer sandwiched between two different electrodes. The absorption layer can either be a layered structure or a homogenous blend of components. The interface between the components is known as a heterojunction. Devices where the components form individual layers have been previously reported, see U.S. Pat. No. 4,164,431; Appl. Phys. Lett., 48, 1986, 183 and Appl. Phys. Lett., 62, 1993, 585. Also known are devices where the components are homogenously blended together forming a dispersed or bulk heterojunction, see Appl. Phys. Lett., 58, 1991, 1062; Appl. Phys. Lett., 64, 1994, 3422; J. Appl. Phys., 78, 1995, 4510; and Nature, 376, 1995, 498.

By using the compounds according to the present invention as part of the absorption layer, light is absorbed promoting an electron from the HOMO energy level to the LUMO energy level forming an exciton. An OPV device operates by dissociating the exciton into an electron and a hole followed by migration of the electron to one electrode while the hole must reach the other. Dissociation only occurs when there is an electric field across the device that is strong enough to overcome the columbic forces that bind the exciton. The field is generated by the difference in work functions of the two electrodes. The materials that form part of the absorption layer also aid dissociation by having different electron affinities and ionisation potentials OFETs where an organic semiconductive material is arranged as a film between a gate-dielectric and a drain and a source electrode, are generally known, e.g., from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these OFETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with monetary value, like stamps, tickets, shares, cheques etc.

Alternatively, the mono-, oligo- and polymers according to the invention may be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., Science, 279, 1998, 835-837.

According to another use, the inventive compounds, materials or films can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 200310021913.

According to another use the materials and polymers according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

The compounds and materials according to the present invention can also be used in cosmetic or pharmaceutical compositions, for example in cosmetic compositions for hair treatment as disclosed in EP 1 498 112 A2.

The invention claimed is:

1. A monomeric, oligomeric or polymeric compound according to formula I1:

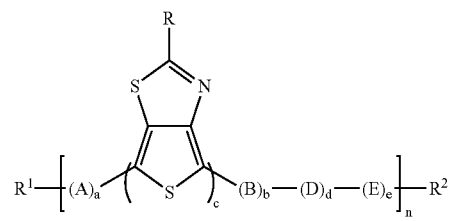

wherein

R is in case of multiple occurrence independently of one another H, halogen, aryl optionally substituted with one or more groups L, heteroaryl optionally substituted with one or more groups L, P-Sp-, P*-Sp-, or straight chain, branched or cyclic alkyl with 1 to 20 C-atoms which is optionally mono- or polysubstituted by F, Cl, Br, I or CN, and wherein one or more non-adjacent $CH_2$ groups are optionally replaced, in each case independently from one another, by —O—, —S—, —NH—, $NR^0$—, —$SiR^0R^{00}$—, —CO—, —COO—, —OCO—, —O—CO—O—, —S—CO—, —CO—S—, —$CX^1$=$CX^2$— or —C≡C— in such a manner that O and/or S atoms are not linked directly to one another;

L is in each case independently F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$, —CO—, —COO—, OCO—, —OCO—O, —S—CO—, —CO—

S—, —CH═CH— or —C≡C— in such a manner that O and/or S atoms are not linked directly to one another;

$X^1$ and $X^2$ are independently of each other H, F, Cl or CN;

P is a polymerizable group selected from $CH_2$═$CW^1$—COO—, $CH_2$═$CW^1$—CO—,

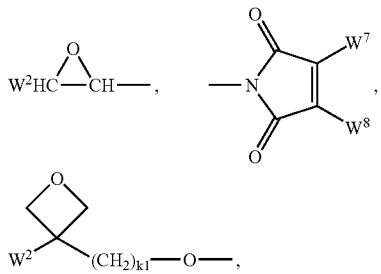

$CH_2$═$CW^2$—(O)$_{k1}$—, $CH_3$—CH═CH—O—, ($CH_2$═CH)$_2$ CH—OCO—, ($CH_2$═CH—$CH_2$)$_2$CH—OCO—, ($CH_2$═CH)$_2$CH—O—, ($CH_2$═CH—$CH_2$)$_2$N—, ($CH_2$═CH—$CH_2$)$_2$N—CO—, HO—$CW^2W^3$—, HS—$CW^2W^3$—, $HW^2$N—, HO—$CW^2W^3$—NH—, $CH_2$═$CW^1$—CO—NH—, $CH_2$═CH—(COO)$_{k1}$-Phe-(O)$_{k2}$—, $CH_2$═CH—(CO)$_{k1}$-Phe-(O)$_{k2}$—, Phe-CH═CH—, HOOC—, OCN—, or $W^4W^5W^6$Si—;

$W^1$ is H, Cl, CN, $CF_3$, phenyl or alkyl with 1 to 5 C-atoms;

$W^2$ and $W^3$ are each independently H or alkyl with 1 to 5 C-atoms;

$W^4$, $W^5$ and $W^6$ are each independently Cl, oxaalkyl with 1 to 5 C-atoms, or oxacarbonylalkyl with 1 to 5 C-atoms;

$W^7$ and $W^8$ are each independently H, Cl or alkyl with 1 to 5 C-atoms;

Phe is 1,4-phenylene which is optionally substituted by one or more groups L;

$k_1$ and $k_2$ are each independently 0 or 1;

P* is a group that can be converted to or substituted by a polymerizable group P;

Sp is a single bond or a group Sp'-X;

Sp' is alkylene with up to 20 C atoms which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH═CH— or —C≡C— in such a manner that O and/or S atoms are not linked directly to one another;

X is —O—, —S—, —CO—, —COO—, —OCO—, —O—COO—, —CO—$NR^0$—, —$NR^0$—CO—, —CO—$NR^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH═N—, —N═CH—, —N═N—, —CH═$CR^0$—, —$CX^1$═$CX^2$—, —CC—, —CH═CH—COO—, —OCO—CH═CH— or a single bond;

A, B and D are independently of each other, and in case of multiple occurrence independently of one another, —$CX^1$═$CX^2$—, —C≡C—, or an arylene or heteroarylene group that is optionally substituted with one or more groups R;

E is thieno[2,3d]thiazole-4,6-diyl or thieno[2,3d]thiazole-6,4-diyl which is optionally substituted in 2-position with R;

a, b, c, d, e are independently of each other 0, 1, 2 or 3, with at least one of c and e being 1;

n is an integer ≧1;

$R^1$ and $R^2$ are independently of each other)Sn($R^0$)$_3$, —B(OR')(OR"), —CH$_2$Cl, —CHO, —CH═CH$_2$, —$SiR^0R^{00}R^{000}$, H, halogen, aryl optionally substituted with one or more groups L, heteroaryl optionally substituted with one or more groups L, P-Sp-, P*-Sp-, or straight chain, branched or cyclic alkyl with 1 to 20 C-atoms which is optionally mono- or polysubstituted by F, Cl, Br, I or CN, and wherein one or more non-adjacent CH$_2$ groups are optionally replaced, in each case independently from one another, by —O—, —S—, —NH—, —$NR^0$—, —$SiR^0R^{00}$—, —CO—, —COO—, —OCO—, —O—CO—O—, —S—CO—, —CO—S—, —$CX^1$═$CX^2$— or —C≡C— in such a manner that O and/or S atoms are not linked directly to one another;

$R^0$, $R^{00}$, $R^{000}$ are independently of each other, H, aryl or alkyl with 1 to 12 C-atoms; and R' and R" are independently of each other H or alkyl with 1 to 12 C-atoms, or OR' and OR" together with the boron atom form a cyclic group having 2 to 20 C atoms;

wherein recurring units are identical or different; and with the provisos that:

(a) homopolymers of 2-nonyl-thieno[3,4-d]thiazole-6,4-diyl are excluded; and (b) n is an integer from 2 to 5000, or n is 1 and one or both of $R^1$ and $R^2$ are halogen, —Sn($R^0$)$_3$, —B(OR')(OR"), —CH$_2$Cl, —CHO, —CH═CH$_2$ or —$SiR^0R^{00}R^{000}$, or n is 1 to 15 and one or both of $R^1$ and $R^2$ are P-Sp-.

2. A compound according to claim 1, wherein at least one of A, B, and D is

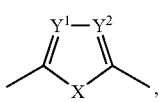

$Y^1$ and $Y^2$ are each CH, CR or N, and X is S or O.

3. A compound according to claim 1, wherein at least one of A, B, and D is thiophene-2,5-diyl which is optionally substituted by one or two groups R different from H, or phenylene-1,4-diyl which is optionally substituted by one, two, three or four groups R different from H.

4. A compound according to claim 1, wherein b is 1 and B is —$CX^1$═$CX^2$—, —C≡C— or a single bond.

5. A compound according to claim 1, wherein R is $C_1$-$C_{20}$-alkyl, $C_1$-$C_{20}$-alkoxy, $C_2$-$C_{20}$-alkenyl, $C_2$-$C_{20}$-alkynyl, $C_1$-$C_{20}$-thioalkyl, $C_1$-$C_{20}$-silyl, $C_1$-$C_{20}$-ester, $C_1$-$C_{20}$-amino, $C_1$-$C_{20}$-fluoroalkyl, optionally substituted aryl, or optionally substituted heteroaryl.

6. A compound according to claim 1, wherein n is an integer from 2 to 5000.

7. A compound according to claim 1, wherein n is 1 and one or both of $R^1$ and $R^2$ are halogen, —Sn($R^0$)$_3$, —B(OR')(OR"), —CH$_2$Cl, —CHO, —CH═CH$_2$ or —$SiR^0R^{00}R^{000}$.

8. A compound according to claim 1, wherein n is 1 to 15 and one or both of $R^1$ and $R^2$ are P-Sp-.

9. A compound according to claim 1, wherein the structure

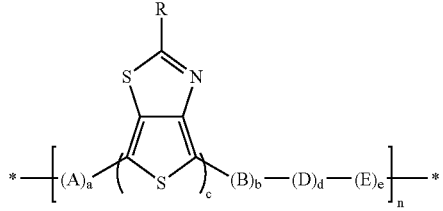

is selected from the following formulae:

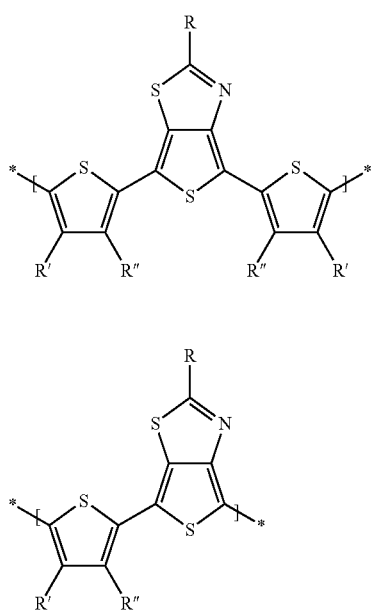

IIa

IIb

IIc

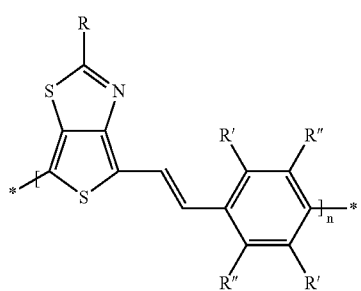

IId

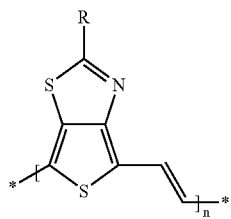

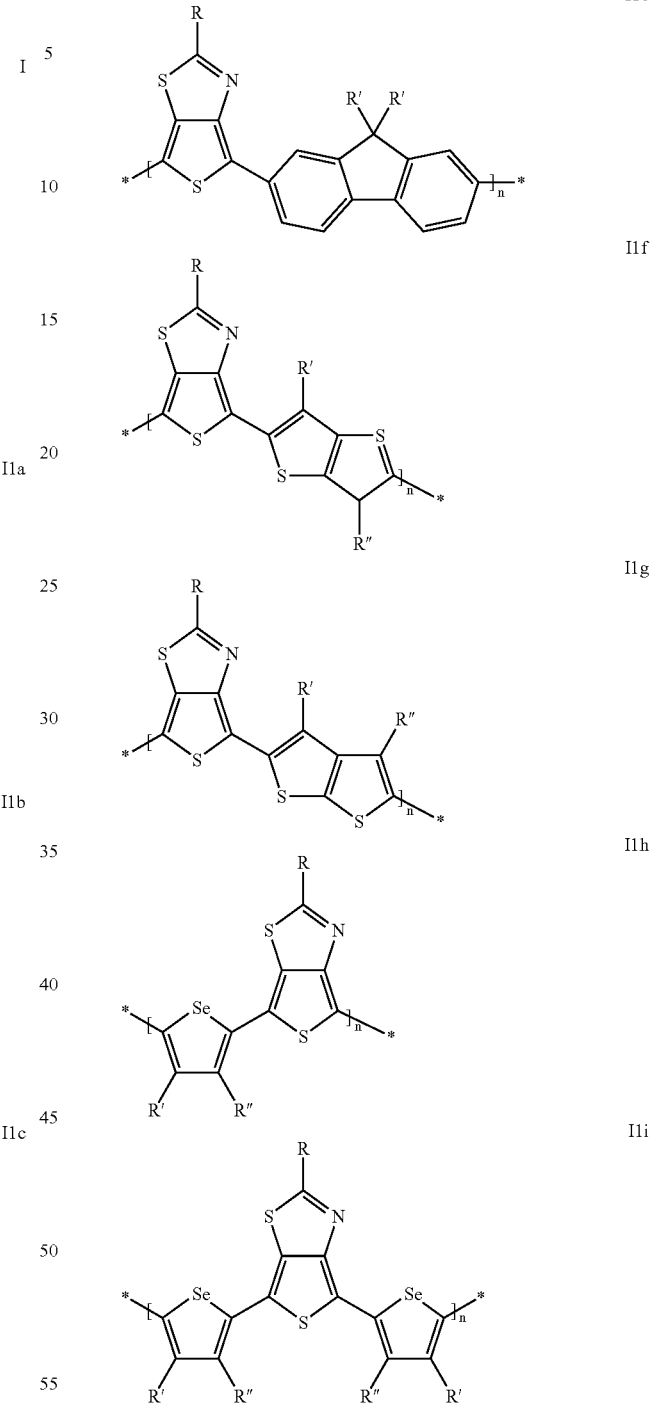

I

IIe

IIf

IIg

IIh

IIi wherein * represents the points of attachment to groups $R^1$ and $R^2$.

10. A polymerizable liquid crystal material comprising one or more compounds according to claim 1 comprising at least one polymerizable group, and optionally comprising one or more further polymerizable compounds, wherein at least one of said compounds according to claim 1 and said further polymerizable compounds is mesogenic or liquid crystalline.

11. An anisotropic polymer film with charge transport properties, wherein said polymer film is obtainable from a polymerizable liquid crystal material according to claim 10 that is aligned in its liquid crystal phase into macroscopically uniform orientation and polymerized or crosslinked to fix the oriented state.

12. A side chain liquid crystal polymer obtained by polymerisation of one or more compounds according to claim 1 or a polymerizable material comprising one or more compounds according to claim 1, or obtained by grafting said one or more compounds or polymerizable material to a polymer backbone in a polymeranaloguous reaction, optionally with one or more additional mesogenic or non-mesogenic comonomers.

13. An optical, electrooptical or electronic components or devices, organic field effect transistors (OFET), integrated circuitry (IC), thin film transistors (TFT), flat panel displays, radio frequency identification (RFID) tags, electroluminescent or photoluminescent devices or components, organic light emitting diodes (OLED), backlights of displays, photovoltaic or sensor devices, charge injection layers, Schottky diodes, planarizing layers, antistatic films, conducting substrates or patterns, electrode materials in batteries, photoconductors, electrophotographic applications, electrophotographic recording, organic memory devices, alignment layers, cosmetic or pharmaceutical compositions, biosensors, or biochips, comprising a charge-transport, semiconducting, electrically conducting, photoconducting or light-emitting material, wherein said material comprises a compound according to claim 1.

14. A semiconducting, electroluminescent or charge transport material, component or device comprising at least one compound according to claim 1, a polymerizable material comprising said at least one compound, or a polymer obtained from said at least one compound.

15. An optical, electrooptical or electronic device, FET, integrated circuit (IC), TFT, OLED or alignment layer comprising a material, component or device according to claim 14.

16. A TFT or TFT array for flat panel displays, radio frequency identification (RFID) tag, electroluminescent display or backlight, comprising a material, component, or device according to claim 14.

17. A security marking or device comprising an RFID tag according to claim 16.

18. A compound according to claim 1, a polymerizable material comprising said compound, or a polymer obtained from said at least one compound which is oxidatively or reductively doped to form a conducting ionic species.

19. A charge injection layer, planarizing layer, antistatic film or conducting substrate or pattern for electronic applications or flat panel displays, comprising a compound, material or polymer according to claim 18.

20. A TFT or TFT array for flat panel displays, radio frequency identification (RFID) tag, electroluminescent display or backlight, comprising an FET, IC, TFT or OLED according to claim 15.

21. A security marking or device comprising a FET according to claim 15.

22. A compound according to claim 1, wherein n is an integer from 100 to 1000.

23. A compound according to claim 1, wherein a and/or b are 1, d is 0, c is 1 or 2, and e is O.

24. A compound according to claim 9, wherein said structure is of formula I1a and I1f, R' is H, and R" is different from H.

25. A compound according to claim 1, wherein arylene or heteroarylene groups for groups A, B and D are selected from 1,4-phenylene, 2,5-pyridine, 2,5-pyrimidine, p,p'-biphenyl, naphthalene-2,6-diyl, thiophene-2,5-diyl, selenophene-2,5-diyl, thiophene-2,5-diyl or selenophene-2,5-diyl, fluorene-2,7-diyl, 2,2'-dithiophene, 2,2'-dithiophene, thieno[2,3-b]thiophene-2,5-diyl, thieno[3,2-b]thiophene-2,5-diyl, fluorinated benzo[1,2-b:4,5-b']dithiophene, 2,5-thiazole, 2,5-thiadiazole, thieno[3,4-d]thiazole-4,6-diyl, thieno[3,4-d]thiazole-6,4-diyl, 2,5-oxazole and 2,5-oxadiazole, all of which are unsubstituted or mono- or polysubstituted by L;

optionally substituted aryl and optionally substituted heteroaryl groups for groups R, $R^1$ and $R^2$ are selected from phenyl, fluorinated phenyl, pyridine, pyrimidine, biphenyl, naphthalene, fluorene, benzo[1,2-b:4,5-b']dithiophene, thieno[3,2-b]thiophene, 2,2-dithiophene, thiazole, thieno[2,3d]thiazole and oxazole, all of which are unsubstituted or mono- or polysubstituted by L; and P* is —OH or —O—Si—$R^O R^{OO} R^{OOO}$.

26. A compound according to claim 25, wherein P is $CH_2$=CH—COO—, $CH_2$=C($CH_3$)—COO—, $CH_2$=CH—, $CH_2$=CH—O—, $(CH_2$=CH$)_2$CH—OCO—, $(CH_2$=CH$)_2$CH—O—,

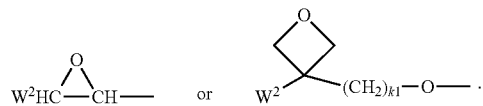

27. A compound according to claim 25, wherein X is —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C— or a single bond.

28. A compound according to claim 25, wherein Sp' is —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^O$R$^{OO}$)$_p$—, p is an integer from 2 to 12, and q is an integer from 1 to 3.

29. A compound according to claim 25, wherein Sp' is ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene or butenylene.

* * * * *

UNITED STATES PATENT AND TRADEMARK OFFICE
CERTIFICATE OF CORRECTION

| | |
|---|---|
| PATENT NO. | : 7,829,658 B2 |
| APPLICATION NO. | : 11/916944 |
| DATED | : November 9, 2010 |
| INVENTOR(S) | : Duffy et al. |

It is certified that error appears in the above-identified patent and that said Letters Patent is hereby corrected as shown below:

Column 21, line 57 reads: "-CH=CR°-, -CX$^1$=CX$^2$-, -CC-," should read -- -CH=CR°-, -CX$^1$=CX$^2$-, -C≡C-, --.

Signed and Sealed this
Twenty-eighth Day of February, 2012

David J. Kappos
*Director of the United States Patent and Trademark Office*